United States Patent
Grein et al.

(10) Patent No.: US 8,617,463 B2
(45) Date of Patent: *Dec. 31, 2013

(54) POLYOLEFIN COMPOSITIONS HAVING IMPROVED OPTICAL AND MECHANICAL PROPERTIES

(75) Inventors: Christelle Grein, Linz (AT); Tonja Schedenig, Enns (AT)

(73) Assignee: Borealis Technology Oy, Porvoo (FI)

( * ) Notice: Subject to any disclaimer, the term of this patent is extended or adjusted under 35 U.S.C. 154(b) by 298 days.

This patent is subject to a terminal disclaimer.

(21) Appl. No.: 12/733,318

(22) PCT Filed: Aug. 26, 2008

(86) PCT No.: PCT/EP2008/061130
§ 371 (c)(1),
(2), (4) Date: Feb. 23, 2010

(87) PCT Pub. No.: WO2009/027389
PCT Pub. Date: Mar. 5, 2009

(65) Prior Publication Data
US 2010/0247375 A1    Sep. 30, 2010

(30) Foreign Application Priority Data

Aug. 31, 2007  (EP) .................................. 07115373

(51) Int. Cl.
*A61L 2/00* (2006.01)
*A61L 2/04* (2006.01)
*A61L 9/00* (2006.01)
*A61L 11/00* (2006.01)
*C23F 11/00* (2006.01)
*A61L 2/08* (2006.01)

(52) U.S. Cl.
USPC .................................. 422/1; 422/26; 422/38

(58) Field of Classification Search
USPC ................................. 422/1, 26, 38
See application file for complete search history.

(56) References Cited

U.S. PATENT DOCUMENTS

| | | | | |
|---|---|---|---|---|
| 5,274,024 | A | * | 12/1993 | Koyama et al. ............... 524/440 |
| 6,022,628 | A | * | 2/2000 | Chatterjee et al. ............ 428/523 |
| 6,231,936 | B1 | | 5/2001 | Kozimor et al. |
| 6,242,535 | B1 | * | 6/2001 | Kagami et al. ................ 525/191 |
| 6,511,755 | B1 | | 1/2003 | Mochizuki et al. |
| 8,173,747 | B2 | * | 5/2012 | Grein et al. .................... 525/191 |
| 2004/0146669 | A1 | | 7/2004 | Gollier et al. |
| 2004/0260001 | A1 | * | 12/2004 | Lin et al. ....................... 524/474 |
| 2006/0051534 | A1 | * | 3/2006 | Iwasaki et al. ................ 428/34.1 |

FOREIGN PATENT DOCUMENTS

| | | |
|---|---|---|
| EP | 1 008 626 A1 | 6/2000 |
| EP | 1 304 218 A1 | 4/2003 |
| EP | 1 484 345 A1 | 12/2004 |
| EP | 1 849 826 A1 | 10/2007 |
| WO | WO03/000754 A1 | 1/2003 |
| WO | WO03/064522 A1 | 8/2003 |
| WO | WO2005/075558 | 8/2005 |
| WO | WO2009/027389 | 3/2009 |

OTHER PUBLICATIONS

"Polypropylene Handbook", edited by Edward P. Moore, Jr., Hanser Publishers,, 1996.
"Polymerization Stereochemistry with Ziegler-Natta Catalysts Containing Dialkylpropane Diethers: A Tool for Understanding Internal/External Donor Relationships"; Mario Carmela Sacchi et al; Macromolecules 1996, 29, 3341-3345.
Polypropylene: An A-Z Reference, J. Karger-Kocsis, Kluwer Academic Publishers, Dordrecht 1999, 60-67.

* cited by examiner

*Primary Examiner* — Regina M Yoo
(74) *Attorney, Agent, or Firm* — Warn Partners, P.C.

(57) ABSTRACT

The invention relates to the use of a polyolefin composition comprising a propylene-ethylene random copolymer having an ethylene content of 0.5-10 wt % and a randomness R of the ethylene distribution in the polymer chain of ≥0.945 for the production of articles having high sterilization resistance.

15 Claims, No Drawings

POLYOLEFIN COMPOSITIONS HAVING IMPROVED OPTICAL AND MECHANICAL PROPERTIES

This application is a National Stage of International Application No. PCT/EP2008/061130, filed Aug. 26, 2008. This application claims priority to European Patent Application No. 07115373.8 filed on Aug. 31, 2007. The disclosures of the above applications are incorporated herein by reference.

The present invention relates to the use of polyolefin compositions for producing articles which have improved optical properties even after subjecting them to a sterilisation step which makes them highly attractive for food and medical applications.

Alpha-olefin polymers such as polyethylene and polypropylene are widely used for packaging applications and increasingly applied also in the medical area and for pharmaceutical packaging where the material is mostly sterilised. Especially suited for these applications are propylene random copolymers. Especially in food packaging and medical applications, films made or essentially consisting of propylene random copolymers have to be sterilised. The most common sterilisation procedures are the use of heat (steam), radiation (beta radiation, electrons or gamma radiation) or chemicals (usually ethylene oxide). This sterilisation procedure affects the mechanical and optical properties, but sometimes also the organoleptic properties of the material significantly.

Steam sterilisation, usually carried out in a temperature range of 120 to 130° C., results mostly in post-crystallisation and physical ageing effects of the polypropylene. Moreover, the material tends to become stiffer and more brittle. Also, optical disturbances are severely increased and significantly increase the haze of transparent articles.

Especially in steam sterilisation, performed at 121° C. for 30 min, the crystallinity of films made of propylene copolymers significantly increases, resulting in a modulus and haze increase together with significant embrittlement. Thus, a reduction of the impact strength is further observed.

In the field of packaging, propylene random copolymers have gained increasing interest due to their improved transparency, relative softness, lower sealing temperature compared to propylene homopolymers and moderate low-temperature impact strength. Nevertheless, the incorporation of comonomers into the propylene polymer chain concentrates stereo defects into the polymer chains leading to intermolecular heterogeneity of the propylene copolymer. Such heterogeneity increases the above outlined drawbacks, especially after performing sterilisation on films made of such propylene copolymer compositions.

In view of the above problems, several proposals have been made to achieve propylene copolymers which can be manufactured into films with improved optical and mechanical properties.

EP 1 008 626 A1 proposes a hollow vessel for heat sterilisation made of a polyolefin resin which is superior in transparency and impact strength and causes minor emission of smell and preserves these properties even after subjecting to heat sterilization with steam. The material is characterized by a haze value difference, between the haze value after sterilization and the haze value before sterilization of 1 to 20%, determined according to ASTM D1330 for a resin specimen of a thickness of 0.5 mm when the heat sterilisation treatment is performed at a temperature of 121° C. for 20 min. The material comprises a rather complicated blend of a polypropylene resin, an ethylene copolymer and propylene-ethylene-1-butene terpolymer.

U.S. Pat. No. 6,231,936 B1 discloses articles such as packaging materials and medical devices having enhanced tolerance to radiation and heat, produced from a blend of from about 99 wt.-% to 50 wt.-% homo- or copolymerised polypropylene and about 1 wt.-% to 50 wt.-% polyethylene produced by single-site catalysis. The polymer blends described in this document typically comprise propylene homopolymer and polyethylene produced by using a metallocene catalyst. However, propylene random copolymers may also be incorporated. The document reports on improving effects as to resistance to embrittlement and coloration when a specific single-site catalysed polyethylene is admixed to polypropylene.

WO 03/064522 A1 discloses a non-rigid or flexible material which is sterilisable using steam at a temperature of at least 121° C. and/or by irradiation wherein the material comprises at least one of a polypropylene having a melting temperature below 145° C. and a modulus in flexure (Emod) of from 25 to 800 MPa and a propylene copolymer having melting temperature of below 145° C. and a modulus in flexure (Emod) of from 25 to 800 MPa and optionally at least one plastomer comprising at least one random copolymer of ethylene and at least one $C_3$ to $C_{10}$ alpha-olefin having a density of from 0.8 to 0.9 g/cm$^3$ and is substantially free of slip agents and anti-blocking agents. The document reports on preservation of a haze transparency index of less than 10% and a gloss brightness index of more than 80% after steam sterilization at a temperature of at least 121° C. From these materials films may be made which are suitable for pharmaceutical and medical applications. No detectable transfer of components contained in the film into a solution which was stored in bags made of that film, is observed.

In view of the above proposals, the improvements in polyolefins are still unsatisfactory for achieving superior characteristics in optical properties after sterilisation.

Therefore, it is an object of the present invention to provide improved articles comprising a polyolefin composition, which articles are sterilisable and which still have satisfactory optical properties after sterilisation, i.e. where the optical properties after sterilisation are less deteriorated (i.e. have a smaller increase in haze and smaller absolute haze value after sterilisation) than with articles from comparable (i.e. comparable ethylene content) known polyolefin compositions.

A still further object of this invention is to provide a process for sterilising an article comprising a polyolefin composition, where the sterilisation process results in a deterioration of optical properties which is less than compared to a sterilisation process for articles comprising known polyolefin compositions.

The present invention is based on the finding that the above discussed disadvantages of the prior art can be overcome by using a polyolefin composition comprising a propylene-ethylene random copolymer having an ethylene content of 0.5-10 wt % and a randomness R of the ethylene distribution in the polymer chain of ≥0.945 for the production of sterilisable articles, having a Δ(haze) value of 100% or less, wherein the sterilisation is carried out at 121° C. for 30 minutes.

The propylene-ethylene random copolymer of which the polyolefin compositions according to the present invention are comprised are characterised by an increased degree of randomness which makes them highly suited for transparent film applications, where the films are sterilised or pasteurised.

The randomness R as used herein is defined as the ratio of the amount of randomly incorporated ethylene to the total amount of ethylene of the propylene-ethylene random copolymer. The total amount of ethylene is the sum of the respective amounts of randomly incorporated ethylene and the amount of ethylene which is incorporated in a blocky manner. Both amounts ("random-ethylene" and "blocky-ethylene") are determined with FTIR. The total concentration of ethylene corresponds to the peak height at 733 cm$^{-1}$. The concentration of blocky-ethylene corresponds to the area of a peak at 720 cm$^{-1}$. The concentration of random-ethylene is calculated as the difference of total ethylene minus blocky-ethylene. The respective amounts of ethlyene are determined from the FTIR spectrum by using calibration curves established with $^{13}$C-NMR.

The Δ(haze) value is calculated by subtracting the haze value after sterilisation from the haze value before sterilisation and dividing the result by the haze value before sterilisation and by multiplying the result by 100. The Δ(haze) value therefore indicates the increase in haze in percent as a result of the sterilisation process.

It is specifically preferred that the inventive articles show a Δ(haze) value of not more than 90%, preferably not more than 80%. Preferred ranges for Δ(haze) may be from 1 to 100%, more preferably 1 to 90%, even more preferably 1 to 80%.

Sterilisation is usually carried out with steam between 120° C. and 130° C., preferably at 121° C. for 10 minutes to 1 hour, preferably for 30 min. Other less aggressive techniques such as pasteurisation usually carried out between 60 and 90° C. for less than 30 min may also be used. Sterilisation by irradiation is a further option.

Sterilisation as used herein is carried out by a treatment with saturated steam at 121° C. for 30 minutes. Where in this application the term "sterilisation" is used, it stands for these conditions mentioned above.

It is the specific finding of the present inventors that superior resistance to sterilisation, especially steam sterilisation can be obtained with articles produced from propylene-ethylene random copolymers when the ethylene content in the copolymer is adjusted to a specific range and when the incorporation of the comonomer is obtained in a particularly homogeneous manner to avoid stereodefects as far as possible.

According to a preferred embodiment of the present invention the propylene-ethylene random copolymer has an ethylene content of 0.8-8 wt %, still more preferably an ethylene content of 1-6 wt %. The sterilisation resistance of articles made from such random copolymers is particularly good.

It is especially preferable that the propylene-ethylene random copolymers used in the present invention show a randomness R of the ethylene distribution in the polymer chain of ≥0.950. A higher R value is indicative for a more homogeneous (i.e. random) incorporation of the ethylene in the polymer chain. The sterilisation resistance generally increases with higher randomness.

According to an advantageous embodiment of the present invention, the randomness R of the ethylene distribution in the polymer chain satisfies the relationship R≥0.887+0.048*CM-0.007*CM$^2$, wherein CM denotes the ethylene content in wt % of the propylene-ethylene random copolymer.

According to a further embodiment of the present invention, a propylene-ethylene random copolymer having an ethylene content of ≤2.6 wt % is used for the production of articles having a Δ(haze) value after sterilisation (120° C. 30 min) of 50% or less. More preferably, a propylene-ethylene random copolymer having an ethylene content of ≤2.5 wt % is used for the production of articles having a Δ(haze) value after sterilisation (120° C. 30 min) of 40% or less, still more preferably of 30% or less. It is particularly preferred to use a propylene-ethylene random copolymer having an ethylene content of ≤2.4 wt % is used for the production of articles having a Δ(haze) value after sterilisation (120° C. 30 min) of 20% or less.

Specific advantages with respect to sterilisation resistance may be obtained if the relationship between comonomer content and melting point of the propylene-ethylene random copolymer satisfies the following relation $T_m \leq 162.5 - 5.4 * CM$, wherein CM denotes the ethylene content in wt % of the propylene-ethylene random copolymer and $T_m$, is the melting temperature in ° C. of the propylene-ethylene random copolymer, determined by differential scanning calorimetry (DSC).

The propylene-ethylene random copolymer according to preferred embodiments of the present invention has a melting temperature below 160° C., more preferred below 150° C. It is preferred that the melting point of the propylene-ethylene random copolymer is at least 125° C., preferably at least 130° C.

Additionally, the propylene-ethylene random copolymer preferably has a melt flow rate MFR$_2$ (ISO 1133, 230 C/2.16 kg) of 0.1 to 100 g/10 min, more preferably of 1 to 30 g/10 min. Propylene random copolymers used in the present invention may specifically have an MFR$_2$ of 1 to 20, preferably of 2 to 12.

It is further preferred that the content of xylene solubles of the inventive alpha-olefin polymer compositions is from 2 to 15 wt %, more preferred from 4 to 10 wt %.

According to a preferred embodiment haze before and after sterilisation is measured according to ASTM D 1003/92 on a cast film prepared from a polyolefin composition as defined according to this invention, having a thickness of 50 μm, wherein the sterilisation is carried out at 121° C. for 30 minutes.

The polyolefin composition may contain commonly used additives like: phenolic antioxidants phosphorus-containing antioxidants, C-radical scavengers, acid scavengers, UV-stabilisers, antistatic agents, nucleating agents, slip agents, and antiblocking agents. These components are well known for the skilled person and may be used in the common amounts and are selected by the skilled person as they are required and according to the respective purpose for which the polyolefin compositions shall be used.

The inventive polyolefin compositions are typically used for obtaining films from which articles for the desired end-use are manufactured. The films may be prepared by any process known to the skilled person, but are preferably produced by a cast process or a blown film process. A roll stack process may also be used.

Cast Film Technology

In this technology for producing polymer films, the molten polymer is extruded through a slot die fed by a (normally single-screw) extruder onto a first cooled roll, the so-called chill-roll. From this roll, the already solidified film is taken up by a second roll (nip roll or take-up roll) and transported to a winding device after trimming the edges.

Blown Film Technology with Water Contact Cooling Ring

In this technology for producing polymer films, the molten polymer is extruded through a tubular die fed by a (usually single-screw) extruder and blown up to a tube. The film tube has contact on the exterior side to a water cooling ring and is cooled down quickly. The already solidified film tube is flattened afterwards by take-up rolls and taken off to a winder.

For a more detailed description see "Polypropylene Handbook", edited by Edward P. Moore, Jr., Hanser Publishers, 1996.

Blown Film Technology with Air Quench

In this manufacturing step for air quenched blown films the film is made using at least a 1.5 blow up ratio, preferably at least a 2.0 blow up ratio, more preferably at least a 2.5 blow up ratio.

The technique of air quenched blown film extrusion is well known for the production of thin plastic films. In an advantageous process, plastics, such as low, linear low and high density polyethylene are extruded through a circular die to form a film. Air is introduced through the centre of the die to maintain the film in the form of a bubble which increases the diameter of the film about 1.5 to 6 fold, after which the bubble is collapsed onto rollers. There are a number of variations of such a process within the skill in the art. Most references to blowing polyolefin films disclose processes used for polyethylene, but these are applicable to the polyolefin compositions of the invention with few modifications within the skill in the art without un-due experimentation.

For instance cooling is often advantageously modified because the art recognises that polypropylene cools and crystallises at a rate different from that of polyethylene.

Therefore, adjustments to the cooling parameters often produce a more stable bubble at desired output rates.

In the formation of blown films, the polymer melt enters a ring-shaped die either through the bottom or side thereof. The melt is forced through spiral grooves around the surface of a mandrel inside the die and extruded through the die opening as a thick-walled tube. The tube is expanded into a bubble of desired diameter and correspondingly decreased thickness as previously described.

Monoaxially Oriented Polypropylene Film (MOPP)

Based on a cast film, a solid-state orientation step below the melting temperature is applied before winding.

Biaxially Oriented Polypropylene Film (BOPP)

Two main technologies are used for this process, which are described in detail in A. Ajji & M. M. Dumoulin, Biaxially oriented polypropylene (BOPP) process, in: J. Karger-Kocsis (Ed.) Polypropylene: An A-Z Reference, Kluwer, Dordrecht 1999, 60-67.

In case the film is produced by a cast process the polymer before film forming is usually subjected to a "controlled rheology" (visbreaking) process. This may be necessary in order to obtain required values for e.g. $MFR_2$, polydispersity index PI and Mw/Mn of the polymer.

Articles, in particular films according to the present invention are advantageously used in packaging applications, for example for food packaging, in particular as food wrapping film.

A particularly preferred application of polyolefin compositions according to the invention are medical articles made from or comprising a material or film according to the present invention. Such a medical article may be designed so that the material or film of the invention at least in part contacts a biological or therapeutic material when the article is used.

Articles, e.g. containers comprising the materials and films of the invention are suitable for e.g. holding and/or storing a therapeutic fluid, forming a conduit or tube guiding a therapeutic fluid, holding and/or storing and/or guiding blood or a constituent thereof or a biological tissue or drugs, proteins or peptides, for example monoclonal antibodies; or collecting a biological fluid or material, more particularly as a drainage bag.

The present invention is also directed to a process for sterilising an article wherein the article comprises a polyolefin composition as defined in accordance with the present invention. Preferably, the sterilisation process is performed at elevated temperature. Still more preferably, the sterilisation is a steam sterilisation and is carried out at a temperature of between 120 to 130° C., most preferably at 121° C. for 30 minutes.

Production of Propylene-Ethylene Random Copolymer

The polymerisation process for the production of the propylene-ethylene random copolymer which is used according to the invention may be a continuous process or a batch process utilising known methods and operating in liquid phase, optionally in the presence of an inert diluent, or in gas phase or by mixed liquid-gas techniques.

Accordingly, the propylene-ethylene random copolymer may be produced by single- or multistage process polymerisation of propylene and ethylene such as bulk polymerisation, gas phase polymerisation, slurry polymerisation, solution polymerisation or combinations thereof using catalysts as described below. Preferably, the copolymer is made either in one or two loop reactor(s) or in a combination of loop and gas phase reactor. Those processes are well known to one skilled in the art.

To obtain the propylene-ethylene random copolymer, it is preferred to use a polymerisation process based on a first polymerisation step in at least one slurry reactor and an optional second polymerisation step preferably comprising at least one gas phase reactor. Preferred slurry reactors are loop reactors.

Preferred reactor arrangements for producing the random propylene copolymer are a single loop reactor or two consecutive loop reactors or a loop reactor followed by a gas phase reactor.

Before the catalyst system is used in the actual polymerisation process it is typically pre-polymerised with small amounts of α-olefins, preferably propylene, in order to enhance catalyst performance and to improve the morphology of the end product.

In the first polymerisation step of the process the optionally prepolymerised catalyst system and a monomer feed comprised of propylene and ethylene is fed into a reactor. The amount of comonomer in the feed can be up to 10 wt %.

Polymerisation can be carried out in the presence of the catalyst system at temperatures lower than 110° C. and pressures in the range of 10 to 100 bar, preferably 30 to 70 bar. The polymerisation is carried out in such conditions that 50 to 100 wt %, preferably 75 to 99 wt % of the end product is polymerised in the first reactor.

In the first polymerisation step a polymer is produced, in which the content of comonomer is in the range of up to 10 wt %. Hydrogen is added, when desired, into the first reactor for adjusting the molecular weight of polymer, as conventional.

After the polymerisation is complete in the first reactor, the reaction medium is optionally transferred into a second reactor, which can be a gas phase reactor. If the second reactor is also a loop reactor, the same range of polymerisation conditions is available as for the first reactor.

In the optional second reactor, 0 to 50 wt %, preferably 1 to 25 wt % of the final polymer is formed. In the second reactor, if it is a gas phase reactor, the polymerisation can be carried out at a temperature of 60 to 90° C. and at a pressure higher than 5 bar, preferably higher than 10 bar. Optionally, propylene and comonomers can be added into the second reactor. Hydrogen can also be added into the gas phase reactor, if desired.

The precise control of the polymerisation conditions and reaction parameters is within the state of the art. After the polymerisation in the first and the optional second reactor is finished, the polymer product is recovered by conventional procedures.

The resulting polymer particles may be pelletised in a conventional compounding extruder with various additives, which are generally used in thermoplastic polymer compositions, such as stabilisers, antioxidants, acid neutralising agents, ultraviolet absorbers, antistatic agents, etc.

The catalyst system, which is preferably used in the polymerisation of the propylene-ethylene random copolymer used in the present invention comprises a group 2 metal and a group 4-6 metal-containing catalyst which comprises an internal electron donor. The catalyst system further comprises a co-catalyst including an aluminium compound; and an external electron donor. Specific examples for catalyst systems useable according to the present invention are disclosed e.g. in WO 03/000754, and EP 1 484 345, which are all incorporated by reference herein.

According to a preferred embodiment of a process for producing such a catalyst, it is provided in form of particles having a predetermined size range. Such a preferred process comprises the steps of:
a) preparing a solution of a complex of a Group 2 metal and an electron donor by reacting a compound of said metal with said electron donor or a precursor thereof in an organic liquid reaction medium;
b) adding said solution of said complex to at least one compound of a transition metal of any of groups 4-6 to produce an emulsion the dispersed phase of which contains more than 50 mol % of the Group 2 metal in said complex;
c) agitating the emulsion, optionally in the presence of an emulsion stabilizer, in order to maintain the droplets of said dispersed phase within an average particle size range of suitably 5 to 200 µm, preferably 10 to 100 µm, even more preferably 20 to 50 µm;
d) solidifying said droplets of the dispersed phase; and
e) recovering the obtained solidified particles of the olefin polymerisation catalyst component.

The Group 2 metal used in the preparation of the catalyst is preferably magnesium and the liquid organic medium for reacting the group 2 metal compound preferably comprises a $C_6$-$C_{10}$ aromatic hydrocarbon, preferably toluene An electron donor compound to be reacted with the Group 2 metal compound preferably is a mono- or diester of an aromatic carboxylic acid or diacid, the latter being able to form a chelate-like structured complex. Said aromatic carboxylic acid ester or diester can be formed in situ by reaction of an aromatic carboxylic acid chloride or diacid dichloride with a $C_2$-$C_{16}$ alkanol and/or diol, and is preferably dioctyl phthalate or bis-(2-ethylhexyl) phthalate.

The reaction for the preparation of the Group 2 metal complex is generally carried out at a temperature of 20 to 80° C., and in case that the Group 2 metal is magnesium, the preparation of the magnesium complex may advantageously be carried out at a temperature of 50 to 70° C.

The compound of a group 4-6 metal is preferably a compound of a Group 4 metal. The Group 4 metal is preferably titanium, and its compound to be reacted with the complex of a Group 2 metal is preferably a halide.

In a still further embodiment of the invention, the compound of a group 4-6 metal can also be selected from Group 5 and Group 6 metals, such as Cu, Fe, Co, Ni and/or Pd compounds.

In a preferred embodiment of the production process of the catalyst component a turbulence minimizing agent (TMA) is added to the reaction mixture before solidifying said particles of the dispersed phase, the TMA being inert and soluble in the reaction mixture under the reaction conditions.

The turbulence minimizing agent (TMA) or mixtures thereof are preferably polymers having linear aliphatic carbon backbone chains, which might be branched with only short side chains in order to serve for uniform flow conditions when stirring. Said TMA is in particular preferably selected from α-olefin polymers having a high molecular weight Mw (as measured by gel permeation chromatography) of about 1 to $40 \times 10^6$, or mixtures thereof. Especially preferred are polymers of α-olefin monomers with 6 to 20 carbon atoms, and more preferably polyoctene, polynonene, polydecene, polyundecene or polydodecene or mixtures thereof, having the molecular weight and general backbone structure as defined before, and most preferably TMA is polydecene.

Usually, said turbulence minimizing agent can be added in any process step before particle formation starts, i.e. at the latest before solidification of the emulsion, and is added to the emulsion in an amount of 1 to 1000 ppm, preferably 5 to 100 ppm and more preferable 5 to 50 ppm, based on the total weight of the reaction mixture.

A preferred embodiment of the process for producing catalysts used for preparing propylene-ethylene random copolymer for the present invention comprises: preparing a solution of a magnesium complex by reacting an alkoxy magnesium compound and an electron donor or precursor thereof in a $C_6$-$C_{10}$ aromatic liquid reaction medium comprising $C_6$-$C_{10}$ aromatic hydrocarbon or a mixture of $C_6$-$C_{10}$ aromatic hydrocarbon and $C_5$-$C_9$ aliphatic hydrocarbon; reacting said magnesium complex with a compound of at least one fourvalent group 4 metal at a temperature greater than 10° C. and less than 60° C., to produce an emulsion of a denser, $TiCl_4$/toluene-insoluble, oil dispersed phase having group 4 metal/Mg mol ratio 0.1 to 10 in an oil disperse phase having group 4 metal/Mg mol ratio 10 to 100; maintaining the droplets of said dispersed phase within the size range 5 to 200 µm by agitation in the presence of an emulsion stabiliser while heating the emulsion to solidify said droplets and adding turbulence minimising agent into the reaction mixture before solidifying said droplets of the dispersed phase, said turbulence minimising agent being inert and soluble in the reaction mixture under the reaction conditions; and solidifying said particles of the dispersed phase by heating and recovering the obtained catalyst particles.

The said disperse and dispersed phases are thus distinguishable from one another by the fact that the denser oil, if contacted with a solution of titanium tetrachloride in toluene, will not dissolve in it. A suitable $TiCl_4$/toluene solution for establishing this criterion would be one having a $TiCl_4$/toluene mol ratio of 0.1 to 0.3. The disperse and dispersed phase are also distinguishable by the fact that the great preponderance of the Mg provided (as complex) for the reaction with the Group 4 metal compound is present in the dispersed phase, as revealed by comparison of the respective Group 4 metal/Mg mol ratios.

In effect, therefore, virtually the entirety of the reaction product of the Mg complex with the Group 4 metal, which is the precursor of the final catalyst component, becomes the dispersed phase, and proceeds through the further processing steps to the final dry particulate form. The disperse phase, still containing a useful quantity of Group 4 metal, can be reprocessed for recovery of that metal.

The production of a two-phase, rather than single-phase reaction product is encouraged by carrying out the Mg complex/Group 4 metal compound reaction at low temperature, specifically above 10° C. but below 60° C., preferably between 20° C. and 50° C. Since the two phases will naturally tend to separate into a lower, denser phase and supernatant lighter phase, it is necessary to maintain the reaction product as an emulsion by agitation, preferably in the presence of an emulsion stabiliser.

The resulting particles from the dispersed phase of the emulsion are of a size, shape (spherical) and uniformity which render the final catalyst extremely effective in olefin polymerisation. This morphology is preserved during the heating to solidify the particles, and of course throughout the final washing and drying steps. It is, by contrast, difficult to the point of impossibility to achieve such morphology through precipitation, because of the fundamental uncontrollability of nucleation and growth, and the large number of variables which affect these events.

The electron donor is preferably an aromatic carboxylic acid ester, particularly favoured esters being dioctyl phthalate and bis-(2-ethylhexyl) phthalate. The donor may conveniently be formed in situ by reaction of an aromatic carboxylic acid chloride precursor with a $C_2$-$C_{16}$ alkanol and/or diol. The liquid reaction medium preferably comprises toluene.

Furthermore, emulsifying agents/emulsion stabilisers can be used additionally in a manner known in the art for facilitating the formation and/or stability of the emulsion. For the said purposes e.g. surfactants, e.g. a class based on acrylic or methacrylic polymers can be used. Preferably, said emulsion stabilizers are acrylic or methacrylic polymers, in particular those with medium sized ester side chains having more than 10, preferably more than 12 carbon atoms and preferably less than 30, and preferably 12 to 20 carbon atoms in the ester side chain. Particular preferred are unbranched $C_{12}$ to $C_{20}$ acrylates such as poly(hexadecyl)-methacrylate and poly(octadecyl)-methacrylate.

It has been found that the best results are obtained when the Group 4 metal/Mg mol ratio of the denser oil is 1 to 5, preferably 2 to 4, and that of the disperse phase oil is 55 to 65. Generally the ratio of the mol ratio Group 4 metal/Mg in the disperse phase oil to that in the denser oil is at least 10.

Solidification of the dispersed phase droplets by heating is suitably carried out at a temperature of 70-150° C., usually at 90-110° C.

The finally obtained catalyst is desirably in the form of particles having an average size range of 5 to 200 μm, preferably 10 to 100, more preferably 20 to 50 μm.

The reagents can be added to the aromatic reaction medium in any order. However it is preferred that in a first step the alkoxy magnesium compound is reacted with a carboxylic acid halide precursor of the electron donor to form an intermediate; and in a second step the obtained product is further reacted with the Group 4 metal. The magnesium compound preferably contains from 1 to 20 carbon atoms per alkoxy group, and the carboxylic acid should contain at least 8 carbon atoms.

Reaction of the magnesium compound, carboxylic acid halide and alcohol proceeds satisfactorily at temperatures in the range 20 to 80° C., preferably 50 to 70° C. The product of that reaction, the "Mg complex", is reacted with the Group 4 metal compound at a lower temperature, to bring about the formation of a two-phase, oil-in-oil, product.

The reaction medium used as solvent can be aromatic or a mixture of aromatic and aliphatic hydrocarbons, the latter one containing preferably 5-9 carbon atoms, more preferably 5-7 carbon atoms, or mixtures thereof. Preferably, the liquid reaction medium used as solvent in the reaction is aromatic and is more preferably selected from hydrocarbons such as substituted and unsubstituted benzenes, preferably from alkylated benzenes, even more preferably from toluene and the xylenes, and is most preferably toluene. The molar ratio of said aromatic medium to magnesium is preferably less than 10, for instance from 4 to 10, preferably from 5 to 9.

The alkoxy magnesium compound group is preferably selected from the group consisting of magnesium dialkoxides, complexes of a magnesium dihalide and an alcohol, and complexes of a magnesium dihalide and a magnesium dialkoxide. It may be a reaction product of an alcohol and a magnesium compound selected from the group consisting of dialkyl magnesiums, alkyl magnesium alkoxides, alkyl magnesium halides and magnesium dihalides. It can further be selected from the group consisting of dialkyloxy magnesiums, diaryloxy magnesiums, alkyloxy magnesium halides, aryloxy magnesium halides, alkyl magnesium alkoxides, aryl magnesium alkoxides and alkyl magnesium aryloxides.

The magnesium dialkoxide may be the reaction product of a magnesium dihalide such as magnesium dichloride or a dialkyl magnesium of the formula $R'_xR''_yMg$, wherein x+y=2 and x and y are in the range of 0.3-1.7 and each one of R' and R" is a similar or different $C_1$-$C_{20}$ alkyl, preferably a similar or different $C_4$-$C_{10}$ alkyl. Typical magnesium alkyls are ethylbutyl magnesium, dibutyl magnesium, dipropyl magnesium, propylbutyl magnesium, dipentyl magnesium, butylpentylmagnesium, butyloctyl magnesium and dioctyl magnesium. Preferably, R' is a butyl group and R" is an octyl group, i.e. the dialkyl magnesium compound is butyl octyl magnesium, most preferably the dialkyl magnesium compound is $Mg[(Bu)_{1.5}(Oct)0.5]$.

Dialkyl magnesium, alkyl magnesium alkoxide or magnesium dihalide can react with a polyhydric alcohol $R(OH)_m$, with m being in the range of 2-4, or a monohydric alcohol ROH or mixtures thereof.

Typical $C_2$ to $C_6$ polyhydric alcohols may be straight-chain or branched and include ethylene glycol, propylene glycol, trimethylene glycol, 1,2-butylene glycol, 1,3-butylene glycol, 1,4-butylene glycol, 2,3-butylene glycol, 1,5-pentanediol, 1,6-hexanediol, 1,8-octanediol, pinacol, diethylene glycol, triethylene glycol, and triols such as glycerol, methylol propane and pentareythritol.

The aromatic reaction medium may also contain a monohydric alcohol, which may be straight or branched chain. Typical $C_1$-$C_5$ monohydric alcohols are methanol, ethanol, n-propanol, iso-propanol, n-butanol, iso-butanol, sec. butanol, tert. butanol, n-amyl alcohol, iso-amyl alcohol, sec. amyl alcohol, tert. amyl alcohol, diethyl carbinol, akt. amyl alcohol, sec. isoamyl alcohol, tert. butyl carbinol. Typical $C_6$-$C_{10}$ monohydric alcohols are hexanol, 2-ethyl-1-butanol, 4-methyl-2-pentanol, 1-heptanol, 2-heptanol, 4-heptanol, 2,4-dimethyl-3-pentanol, 1-octanol, 2-octanol, 2-ethyl-1-hexanol, 1-nonanol, 5-nonanol, diisobutyl carbinol, 1-decanol and 2,7-dimethyl-2-octanol. Typical >$C_{10}$ monohydric alcohols are n-1-undecanol, n-1-dodecanol, n-1-tridecanol, n-1-tetradecanol, n-1-pentadecanol, 1-hexadecanol, n-1-heptadecanol and n-1-octadecanol. The monohydric alcohols may be unsaturated, as long as they do not act as catalyst poisons.

Preferable monohydric alcohols are those of formula ROH in which R is a $C_2$-$C_{16}$ alkyl group, most preferably a $C_4$-$C_{12}$ alkyl group, particularly 2-ethyl-1-hexanol or 1-octanol.

Preferably, essentially all of the aromatic carboxylic acid ester is a reaction product of a carboxylic acid halide, preferably a dicarboxylic acid dihalide, more preferably an unsaturated, dicarboxylic acid dihalide, most preferably phthalic acid dichloride, with the monohydric alcohol.

The compound of a fourvalent Group 4 metal containing a halogen is preferably a titanium tetrahalide. Equivalent to titanium tetrahalide is the combination of an alkoxy titanium halide and a halogenation agent, which are able to form a titanium tetrahalide in situ. The most preferred halide is the chloride.

As is known, the addition of at least one halogenated hydrocarbon during the catalyst preparation process can lead to further improved catalytic activity. Reactive halogenated hydrocarbons preferably have the formula $R'''X'''_n$ wherein $R'''$ is a $C_1$-$C_{20}$ hydrocarbyl group, particularly a $C_1$-$C_{10}$ aliphatic hydrocarbyl group, $X'''$ is a halogen, preferably chlorine, and n is an integer from 1 to 4.

Such chlorinated hydrocarbons include monochloromethane, dichloromethane, trichloromethane (chloroform), tetrachloromethane, monochloroethane, (1,1)-dichloroethane, (1,2)-dichloroethane, (1,1,1)-trichloroethane, (1,1,2)-trichloroethane, (1,1,1,2)-tetrachloroethane, (1,1,2,2)-tetrachloroethane, pentachloroethane, hexachloroethane, 1-chloropropane, 2-chloropropane, (1,2)-dichloropropane, (1,3)-dichloropropane, (1,2,3) trichloropropane, 1-chlorobutane, 2-chlorobutane, isobutyl chloride, tert. butyl chloride, (1,4)-dichlorobutane, 1-chloropentane and (1,5)-dichloropentane. The chlorinated hydrocarbons may also be unsaturated, provided that the unsaturation does not act as catalyst poison in the final catalyst.

In the above formula, $R'''$ is preferably a $C_1$-$C_{10}$ alkyl group, $X'''$ is preferably chlorine and n is preferably 1 or 2. Preferred compounds include butyl chloride (BuCl), dichloroalkanes such as (1,4)-dichlorobutane, and tertiary butyl chloride.

Though the catalyst preparation as described herein can be carried out batchwise, semi-continuously or continuously. In such a semi-continuous or continuous process, the solution of the complex of the group 2 metal and said electron donor, which is prepared by reacting the compound of said metal with said electron donor in an organic liquid reaction medium, is mixed with at least one compound of a transition metal, which might be solved in the same or different organic liquid reaction medium. The so obtained solution is then agitated, possibly in the presence of an emulsion stabiliser, and then the agitated emulsion is fed into a temperature gradient reactor, in which the emulsion is subjected to a temperature gradient, thus leading to solidifying the droplets of a dispersed phase of the emulsion. The TMA is preferably contained in the solution of the complex or added to the solution before feeding the agitated solution to the temperature gradient reactor.

When feeding said agitated emulsion to the temperature gradient reactor, an inert solvent, in which the droplets are not soluble, can additionally be fed into that gradient reactor in order to improve the droplet formation and thus leading to a uniform grain size of the particles of the catalyst component, which are formed in the temperature gradient reactor when passing through said line. Such additional solvent might be the same as the organic liquid reaction medium, which is used for preparing the solution of the complex of the group 2 metal as explained above in more detail.

The solidified particles of the catalyst component can subsequently be recovered by an in-stream filtering unit and are preferably subjected to washing in order to remove unreacted starting components.

The recovered particulate product is washed at least once, preferably at least twice, most preferably at least three times with a hydrocarbon, which preferably is selected from aromatic and aliphatic hydrocarbons, preferably with toluene, particularly with hot (e.g. 90° C.) toluene, which may include a small amount, preferably about 0.01-10 vol % of $TiCl_4$ or an alkyl aluminium chloride, such as diethyl aluminium chloride (DEAC), in it. A further washing step is advantageously performed with heptane, most preferably with hot (e.g. 90° C.) heptane, and a still further washing step with pentane. A washing step typically includes several substeps. A favoured washing sequence is, for example, one washing step with toluene at 90° C., two washing steps with heptane at 90° C. and one or two washing steps with pentane at room temperature.

Finally, the washed catalyst component is dried, e.g, by evaporation or flushing with nitrogen.

After washing and drying the catalyst can be stored for further use or can be subjected to further treatment steps or can immediately be fed to a polymerisation reactor.

The catalyst system which is used according to the present invention also comprises an aluminium alkyl compound, preferably of the general formula $AlR_{3-n}X_n$ wherein R stands for straight chain or branched alkyl group having 1 to 20, preferably 1 to 10 and more preferably 1 to 6 carbon atoms, X stands for halogen and n stands for 0, 1, 2 or 3, which aluminium alkyl compound is added, and brought into contact with the droplets of the dispersed phase of the agitated emulsion before recovering the solidified particles of the catalyst.

It is further preferred that at least a part of the aluminium compound is added, in pure form or in the form of a solution, from shortly before the beginning of the emulsion formation until adding it to the washing liquid, e.g. toluene, in such an amount that the final Al content of the particles is from 0.05 to 1 wt %, preferably 0.1 to 0.8 wt % and most preferably 0.2 to 0.7 wt % by weight of the final catalyst particles. The most preferred Al content may vary depending upon the type of the Al compound and on the adding step. For example, in some cases the most preferred amount may be 0.1 to 0.4 wt %.

Still further, preferably tri-($C_1$-$C_6$)-alkyl aluminium compounds are used, triethylaluminium being most preferred.

In Ziegler-Natta catalysts aluminium alkyl compounds are used as cocatalysts, i.e. for activating the catalyst. During activation of polypropylene catalysts, alkyl aluminium does not only reduce and alkylate the active metal, but it has also influence on the donor composition. It is well-known that alkyl aluminium compounds can remove carboxylic acid esters, which are used as internal donors. Simultaneously, external donors can be fixed on the catalyst. Typically, triethyl aluminium (TEAl) is used as cocatalyst and silanes as external donors as is disclosed e.g. in articles Sacci, M. C.; Forlini, F.; Tritto I. And Locatelli P., Macromolecules, 1996, 29, 3341-3345 and Sacci, M. C.; Tritto, I.; Shan, C. and Mendichi, R., Macromolecules, 1991, 24, 6823-6826.

In the catalysts used in the present invention, the internal donor, preferably bis-(2-ethylhexyl) phthalate (DOP), can be significantly extracted from the catalyst with the use of the alkyl aluminium compound. The extraction level is dependent on the concentration of the aluminium alkyl. The higher the concentration, the more of the internal donor can be extracted. Further, the addition of the external donor together with aluminium alkyl improves the donor exchange. The longer the reaction time is, the more external donor is bound on the catalyst.

Particularly preferred external donors are any of the following: cyclohexyl methyl dimethoxy silane, dicyclopentyl dimethoxy silane, diisopropyl dimethoxysilane, di-isobutyl dimethoxysilane and di-tert.-butyl dimethoxysilane. Most preferred are cyclohexyl methyl dimethoxy silane and dicyclopentyl dimethoxy silane, cyclohexyl methyl dimethoxy silane being particularly preferred.

It is preferred, that a solution containing alkyl aluminium and external donor in an organic solvent, e.g. pentane, are added to the catalyst after solidification of the catalyst particles.

The catalyst which is obtained by the above described process is a non-supported Ziegler-Natta catalyst. Non-supported catalysts do not use any external carrier, contrary to conventional catalysts, e.g. e.g. conventional Ziegler-Natta catalysts, which are e.g. supported on silica or $MgCl_2$.

Further preferred embodiments of the catalyst system production include all preferred embodiments as described in WO 03/000754.

1. MEASUREMENT METHODS a) Melt Flow Rate

The melt flow rate is determined according to ISO 1133 and it is indicated in g/10 min. The MFR is an indication of the flowability and thus the processability of the polymer. The higher the melt flow rate, the lower the viscosity of the polymer. The MFR of propylene compositions and polymers is measured with a load of 2.16 kg at 230° C.

b) Melting Temperature $T_m$

The melting temperature is determined by differential scanning calorimetry (DSC) according to ISO 3146; it is taken as the maximum of the melting peak over the temperature during the second heating scan of a sequence heating/cooling/heating of +10/−10/+10 K/min between ambient temperature and 210° C.

c) Ethylene Content

The ethylene content was determined using Fourier transform infrared spectroscopy (FTIR) using the peak height at 733 $cm^{-1}$ as a measure of ethylene content. The measurement is carried out on compression moulded films of 50 μm thickness, using a calibration curve e) Haze

Haze of cast films was measured according to ASTM D 1003/92 on 50 μm thick cast films.

f) Δ(Haze)

The value of Δ(haze) is obtained by dividing the difference between the haze after sterilisation and the haze before heat sterilisation with the haze before heat sterilisation, multiplied by 100.

The haze values are measured according to the standard which is appropriate for the respective article (e.g. ASTM D 1003/92 for films)

f) Randomness R

The randomness R as used herein is defined as the ratio of the amount of randomly incorporated ethylene to the total amount of ethylene of the propylene-ethylene random copolymer. The total amount of ethylene is the sum of the respective amounts of randomly incorporated ethylene and the amount of ethylene which is incorporated in a blocky manner. Both amounts ("random-ethylene" and "blocky-ethylene") are determined with FTIR. The total concentration of ethylene corresponds to the peak height at 733 $cm^{-1}$. The concentration of blocky-ethylene corresponds to the area of a peak at 720 $cm^{-1}$. The concentration of random-ethylene is calculated as the difference of total ethylene minus blocky-ethylene. The respective amounts of ethlyene are determined from the FTIR spectrum by using calibration curves established with $^{13}$C-NMR.

The area of a peak at 720 $cm^{-1}$ is determined in the following way:
- a first spectrum of the sample of which the Randomness is to be determined is recorded
- a second spectrum of a sample which consists of the XCU (insoluble in cold xylene) portion of a random copolymer (the copolymer having ca. 4 wt % ethylene) is recorded. The XCU portion of a random copolymer contains only randomly incorporated ethylene.
- The second spectrum is electronically increased/decreased, such that its peak at 733 $cm^{-1}$ has the same height as the first spectrum.
- The thus modified second spectrum is subtracted from the first spectrum.
- The peak area of a peak at 720 $cm^{-1}$ of the first spectrum can now be measured and the corresponding block-ethylene content determined with the aid of a calibration curve.

2. EXAMPLES

(a) Production of Copolymers and Properties Thereof

Propylene bulk polymerisation was carried out in a stirred 20 l tank reactor. About 3.6 ml triethyl aluminium (TEAl) as a co-catalyst, ca 0.48 ml cyclohexyl methyl dimethoxy silane (CHMDMS) as an external donor and 120 ml n-pentane were mixed and allowed to react for 5 minutes. Half of the mixture was then added to the polymerisation reactor and the other half was mixed with about 80 mg of the catalyst. After additional 5 minutes the catalyst/TEAl/donor/n-pentane mixture was added to the reactor. The Al/Ti mole ratio was 250 mol/mol and the Al/CHMDMS mole ratio was 10 mol/mol. 280 mmol hydrogen and 5600 g propylene were introduced into the reactor and the temperature was raised within ca 15 minutes to the polymerisation temperature of 68° C. The polymerisation time at 68° C. was 60 minutes, after which the polymer formed was taken out from the reactor.

The following additives were added to the propylene random copolymers used for the production of the films according to the invention and to the polymers used for the production of the comparative films before film production: 0.05 wt. % calcium stearate, 0.05 wt. % Irganox® 1010, 0.05 wt. % Irgafos® 168, 0.2 wt. % erucic acid amide, and 0.18 wt. % synthetic silica (Sylobloc® 45).

The obtained propylene copolymers were visbroken before film production from MFR 1.5 g/10 min to approximately MFR 8 g/10 min using 2,5-dimethyl-2,5-di-(tert. butylperoxy)hexane (Triganox® 101).

Cast films were produced on a single screw extruder with a barrel diameter of 30 mm and a slot die of 200×0.5 mm in combination with a chill- and take-up roll. Melt temperature was 260° C. in the die. The chill roll and the take-up roll were kept at 15° C. A film thickness of 50 μm was adjusted through the ratio between the extruder output (4.5 kg/h) and take-off speed (10.5 m/min).

(b) Preparation of the Catalyst

Preparation of the Mg-Complex

In a 150 l steel reactor 19.4 kg of 2-ethyl hexane-1-ol were added at 20° C. 56.0 kg of a 20% BOMAG A (Tradename) [$Mg(Bu)_{1.5}(Oct)_{0.5}$] solution in toluene were then slowly added to the well stirred alcohol. The temperature of the mixture was then increased to 60 C, and the reactants were allowed to react for 30 minutes at this temperature. After addition of 5.5 kg of 1,2-phthaloyl dichloride, the reaction mixture was stirred at 60° C. for another 30 minutes to ensure complete reaction. 13.8 kg of 1-chloro butane were then added at 60° C., and stirring at this temperature was continued for 30 minutes. After cooling to room temperature a yellow solution was obtained.

Preparation of the Catalyst Component 100 ml titanium tetrachloride were placed in a 1 l reactor equipped with a mechanical stirrer. Mixing speed was adjusted to 110 rpm. After addition of 50 ml n-heptane, 180 ml of the Mg-complex solution was added to the well-stirred reaction mixture at 25° C. within 10 minutes. After addition a dark red emulsion was formed. After addition of the Mg-complex, 15 ml of toluene solution containing 45 mg polydecene was added. Then 10 ml of Viscoplex® 1-254 was added. 10 min after addition the temperature of the reactor was increased to 90° C. and stirring at this temperature was continued for 30 min. After settling and filtering, the solid was washed with 200 ml of toluene containing 0.1 vol % diethyl aluminium chloride at 90° C. for 35 min. Then the washings were continued with two times 150 ml heptane for 10 min. Then the catalyst was taken out from the reactor to a separate drying vessel as a slurry with 100 ml of heptane. Finally, the solid catalyst was dried at 60° C. by purging nitrogen through the catalyst bed.

In the comparative examples propylene random copolymers were produced in the same manner as the inventive polymers except that a conventional polymerization catalyst (ZNM1) was used. ZNM1 is commercially available from Basell Polyolefine GmbH, Frankfurt, Germany under the tradename "Avant ZN M1®".

ZNM1 catalyst is a conventional supported Ziegler Natta catalyst.

Reference Example 1 uses a non-supported catalyst according to the present invention.

Reference Example 2 uses a ZNM1 catalyst.

TABLE 1

| | Donor | MFR [g/10 min] | Tm [° C.] | C2-content [wt %] | Randomness R | Haze before sterilisation [%] | Haze after sterilisation [%] | Δ(haze) [%] |
|---|---|---|---|---|---|---|---|---|
| Ref. Ex. 1 | CHMDMS | 8 | 162.9 | 0 | — | 2.2 | 3.8 | 72.7 |
| Example 1 | CHMDMS | 7.9 | 153.8 | 1.6 | 0.952 | 1.9 | 2.2 | 15.8 |
| Example 2 | CHMDMS | 7.5 | 146.6 | 2.4 | 0.972 | 2.3 | 2.7 | 17.4 |
| Example 3 | CHMDMS | 7.5 | 145 | 2.8 | 0.977 | 1.8 | 3 | 66.7 |
| Example 4 | CHMDMS | 8.2 | 144 | 3.5 | 0.979 | 2.7 | 4.8 | 77.8 |
| Example 5 | CHMDMS | 8.6 | 138.2 | 4.3 | 0.967 | 2.4 | 4.1 | 70.8 |
| Example 6 | CHMDMS | 8.4 | 132.3 | 5.2 | 0.958 | 2.8 | 4 | 42.9 |
| Ref. Ex. 2 | CHMDMS | 8.6 | 163.7 | 0 | — | 2.4 | 4 | 66.7 |
| Comp. Ex. 1 | CHMDMS | 7.4 | 154.7 | 1.6 | 0.913 | 2.2 | 3.4 | 54.5 |
| Comp. Ex. 2 | CHMDMS | 7.6 | 147.4 | 2.4 | 0.941 | 2 | 3.2 | 60.0 |
| Comp. Ex. 3 | CHMDMS | 8.5 | 145.2 | 3.3 | 0.915 | 1.9 | 7.7 | 305.3 |
| Comp. Ex. 4 | CHMDMS | 7.4 | 140.9 | 4.3 | 0.918 | 2.1 | 16.1 | 666.7 |
| Comp. Ex. 5 | CHMDMS | 7.2 | 136.3 | 5 | 0.900 | 2.4 | 15.7 | 554.2 |

We claim:

1. Use of a polyolefin composition comprising a propylene-ethylene random copolymer having an ethylene content of ≤2.4 wt % and a randomness R of an ethylene distribution in a polymer chain of ≥0.945 for a production of sterilisable articles, having a Δ(haze) value of 100% or less, wherein a sterilization is carried out at 121° C. for 30 minutes and wherein further the randomness R of the ethylene distribution in the polymer chain satisfies a relationship R≥0.887+0.048*CM−0.007*CM$^2$, wherein CM denotes the ethylene content in wt % of the propylene-ethylene random copolymer.

2. Use according to claim 1, wherein the propylene-ethylene random copolymer has an ethylene content of 0.8-8 wt %.

3. Use according to claim 1, wherein the propylene-ethylene random copolymer has a randomness R of the ethylene distribution in the polymer chain of ≥0.950.

4. Use according to claim 1, wherein the Δ (haze) value is 50% or less.

5. Use according to claim 1, wherein the propylene-ethylene random copolymer has a melting temperature Tm in ° C., determined by differential scanning calorimetry (DSC), satisfying a relationship Tm≤162.5-5.4*CM, wherein CM denotes the ethylene content in wt % of the propylene-ethylene random copolymer.

6. Use according to claim 1, wherein the propylene-ethylene random copolymer has a melting temperature Tm of not less than 125° C. and below 160° C.

7. Use according to claim 1, wherein the polyolefin composition used for the sterilisable articles is selected such that a 50 μm thickness cast film meets a haze value of less than 100% as measured before and after sterilization as measured according to ASTM D 1003.

8. Use according to claim 1, wherein the sterilisable article is a blown film or cast film.

9. Use according to claim 1, wherein the article is for food packaging or a medical article.

10. Use according to claim 1, wherein the article is selected from the group consisting of a food wrapping film and a container, e.g. a conduit or a tube, for holding and/or storing and/or guiding a therapeutic fluid, and an article for holding and/or storing and/or guiding blood or a constituent thereof.

11. Use according to claim 1, wherein the Δ (haze) value is 40% or less.

12. Use according to claim 1, wherein the Δ (haze) value is 30% or less.

13. Use according to claim 1, wherein the Δ (haze) is 20% or less.

14. Use of a polyolefin composition comprising a propylene-ethylene random copolymer having an ethylene content of ≤2.5 wt % and a randomness R of an ethylene distribution in a polymer chain of ≥0.945 for a production of sterilisable articles, having a Δ (haze) value of 40% or less, wherein a sterilization is carried out at 121° C. for 30 minutes and wherein further the randomness R of the ethylene distribution in the polymer chain satisfies a relationship R≥0.887+0.048*CM−0.007*CM$^2$, wherein CM denotes the ethylene content in wt % of the propylene-ethylene random copolymer.

15. Use according to claim 14, wherein the propylene-ethylene random copolymer has a randomness R of the ethylene distribution in the polymer chain of ≥0.950.

* * * * *